United States Patent
Lee et al.

(10) Patent No.: US 9,747,563 B2
(45) Date of Patent: Aug. 29, 2017

(54) APPARATUS AND METHOD FOR MATCHING LARGE-SCALE BIOMEDICAL ONTOLOGIES

(71) Applicant: UNIVERSITY-INDUSTRY COOPERATION GROUP OF KYUNG HEE UNIVERSITY, Yongin-si (KR)

(72) Inventors: Sung-Young Lee, Seongnam-si (KR); Muhammad Bilal Amin, Yongin-si (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 737 days.

(21) Appl. No.: 14/091,689

(22) Filed: Nov. 27, 2013

(65) Prior Publication Data
US 2015/0149191 A1    May 28, 2015

(51) Int. Cl.
*G06Q 10/06* (2012.01)
*G06Q 50/22* (2012.01)

(52) U.S. Cl.
CPC .......... *G06Q 10/063* (2013.01); *G06Q 50/22* (2013.01)

(58) Field of Classification Search
None
See application file for complete search history.

(56) References Cited

U.S. PATENT DOCUMENTS

| 2005/0267772 | A1 | 12/2005 | Nielsen et al. |
| 2010/0066748 | A1 | 3/2010 | Bivolarski et al. |
| 2012/0059926 | A1 | 3/2012 | Jung et al. |
| 2014/0279805 | A1* | 9/2014 | Pangborn .............. H04L 47/621 706/47 |

FOREIGN PATENT DOCUMENTS

| KR | 10-2010-0120905 A | 11/2010 |
| KR | 10-2012-0071645 A | 7/2012 |
| KR | 10-2012-0118611 A | 10/2012 |

OTHER PUBLICATIONS da Silva, Fabricio Alves Barbosa, and Isaac D. Scherson. "Improving parallel job scheduling using runtime measurements." Workshop on Job Scheduling Strategies for Parallel Processing. Springer Berlin Heidelberg, 2000.*
Feitelson, Dror G. "Job scheduling in multiprogrammed parallel systems." IBM Research Report RC 1790 (1997).*
Groγ, Anika, et al. "On Matching Large Life Science Ontologies in Parallel." Data Integration in the Life Sciences, 2010.

* cited by examiner

*Primary Examiner* — Anna Skibinsky

(57) ABSTRACT

An ontology matching apparatus for large-scale biomedical ontologies according to the present invention is provided, and the ontology matching apparatus includes a preprocessing unit configured to classify received candidate ontologies into one or more ontology subsets to generate ontology subsets, a distribution processing unit configured to divide the generated ontology subsets by virtue of a distribution algorithm, apply a matching algorithm to the divided ontology subsets to generate matching threads, and deliver the generated matching threads to individual cores of participating nodes, and an aggregating unit configured to collect and sum matching results generated by the individual cores performing matching operations based on the matching threads to generate an ontology mapping.

17 Claims, 8 Drawing Sheets

APPARATUS AND METHOD FOR MATCHING LARGE-SCALE BIOMEDICAL ONTOLOGIES

BACKGROUND

1. Field

The following description relates to ontology matching of large-scale biomedical ontologies, more particularly, parallel matching and distribution process of the ontology matching.

2. Description of the Related Art

In recent years, as semantic web tools are applied to biomedical field, many advantages are brought in return. In particular, ontologies in the biomedical systems are frequently used for standardization of biomedical information, knowledge sharing, and reusability. As a result, ontologies are applied to fields like Gene Ontology (GO), National Cancer Institute Thesaurus (NCI), Foundation Model of Anatomy (FMA), and Systemized Nomenclature of Medicine Clinical Terms (SNOMED CT). As described above, various researches effectively apply the ontology to the biomedical field, and researches for providing the already developed ontology with the durability are also made.

The ontologies in the biomedical field are very complicated and large-scale because of the ever-evolving medical data. This complexity and size becomes an obstacle to integration and information processing interoperability. The Open Biomedical Ontologies (OBO) consortium is trying to solve this obstacle by introducing a strategy for ontology evolution. Biomedical ontologies include overlapping information. This overlapping information is necessary for the integration and information processing interoperability of biomedical systems. A relation between different candidate ontologies is referred to as ontology mapping or alignment. The candidate ontologies for mapping procedure of establishing the relation, and the procedure for finding the mapping to establish the relation between different ontologies is referred to as ontology matching.

The ontology matching procedure for finding the ontology mapping on the large-scale biomedical ontology requires two-phase operational complexity and excessive operation jobs. Referring to "On Matching Large Life Science Ontologies in Parallel" published in *Data Integration in the Life Sciences* (2010), the ontology matching is calculated by the Cartesian product between two candidate ontologies. This job requires a resource-based matching algorithm. The excessive operation jobs due to the two-phase operational complexity in the mapping procedure may cause a delay, and the delay of the mapping result causes the ontology mapping for the biomedical system to ineffectively perform the processing within a processing due time.

SUMMARY

The following description relates to an ontology matching apparatus and an ontology matching method of large-scale biomedical ontologies, which performs parallel matching for improved performance over multicore parallel commodity hardware.

In an aspect, an ontology matching apparatus for large-scale biomedical ontologies according to the present invention includes a preprocessing unit configured to classify received candidate ontologies into one or more ontology subsets, configured to divide the candidate ontology subsets by virtue of matching algorithms, wherein the subsets are distributed and matched over multi-core hardware in a distributed environment for parallel matching by utilizing thread-level parallelism by matching threads; and an aggregating unit configured to collect and accumulate matching results generated by the individual cores performing matching operations based on the matching threads to generate an ontology mapping. The ontology matching apparatus may further include an ontology storing unit configured to store serialized ontology subsets, and provide the stored serialized ontology subsets to the preprocessing unit when candidate ontologies that are the same as the received candidate ontologies are received.

The preprocessing unit may serialize the generated ontology subsets into a binary form to generate serialized ontology subsets, and reconfigure the serialized ontology subsets received from the ontology-storing unit through deserialization to generate ontology subsets. The matching threads may include one or more matching requests corresponding to the participating nodes in one-to-one relation, one or more matching jobs corresponding to the individual cores in one-to-one relation provided in the participating nodes corresponding to the matching requests in one-to-one relation, and one or more matching tasks performing the matching operations in the individual cores. The maximum number of matching requests may not exceed the number of participating nodes, and the maximum number of matching jobs may not exceed the number of individual cores among all the participating nodes. The matching jobs may be independent of other matching jobs and the matching requests operating in other participating nodes.

When the candidate ontologies are received, the distribution processing unit may confirm the number of participating nodes and the number of individual cores provided in the participating nodes available, apply the number of the participating nodes and the number of the individual cores to a distribution algorithm to set the number of distributions, and divide the ontology subsets in consideration of the set number of distributions, and apply the matching algorithm to the divided ontology subsets to generate the matching threads including matching requests, matching jobs, and matching tasks.

In another aspect, an ontology matching method, according to the present invention, first classifies received candidate ontologies into one or more ontology subsets. The generated ontology subsets are then divided by a distribution algorithm, and a matching algorithm is applied to the divided ontology subsets to generate matching threads. When the matching threads are generated, the generated matching threads are delivered to individual cores of participating nodes. Matching results generated by the individual cores performing matching operations based on the matching threads are then collected and summed to generate an ontology mapping.

The ontology matching method according to the present invention confirms the number of participating nodes and the number of individual cores of each of the participating nodes, and applies the numbers of the participating nodes and individual cores to a distribution algorithm to set the number of distributions. The ontology subsets are then divided in consideration of the set number of distributions, and a matching algorithm is applied to generate matching threads including matching requests, matching jobs, and matching tasks.

Other features and aspects will be apparent from the following detailed description, the drawings, and the claims.

Figure 1:
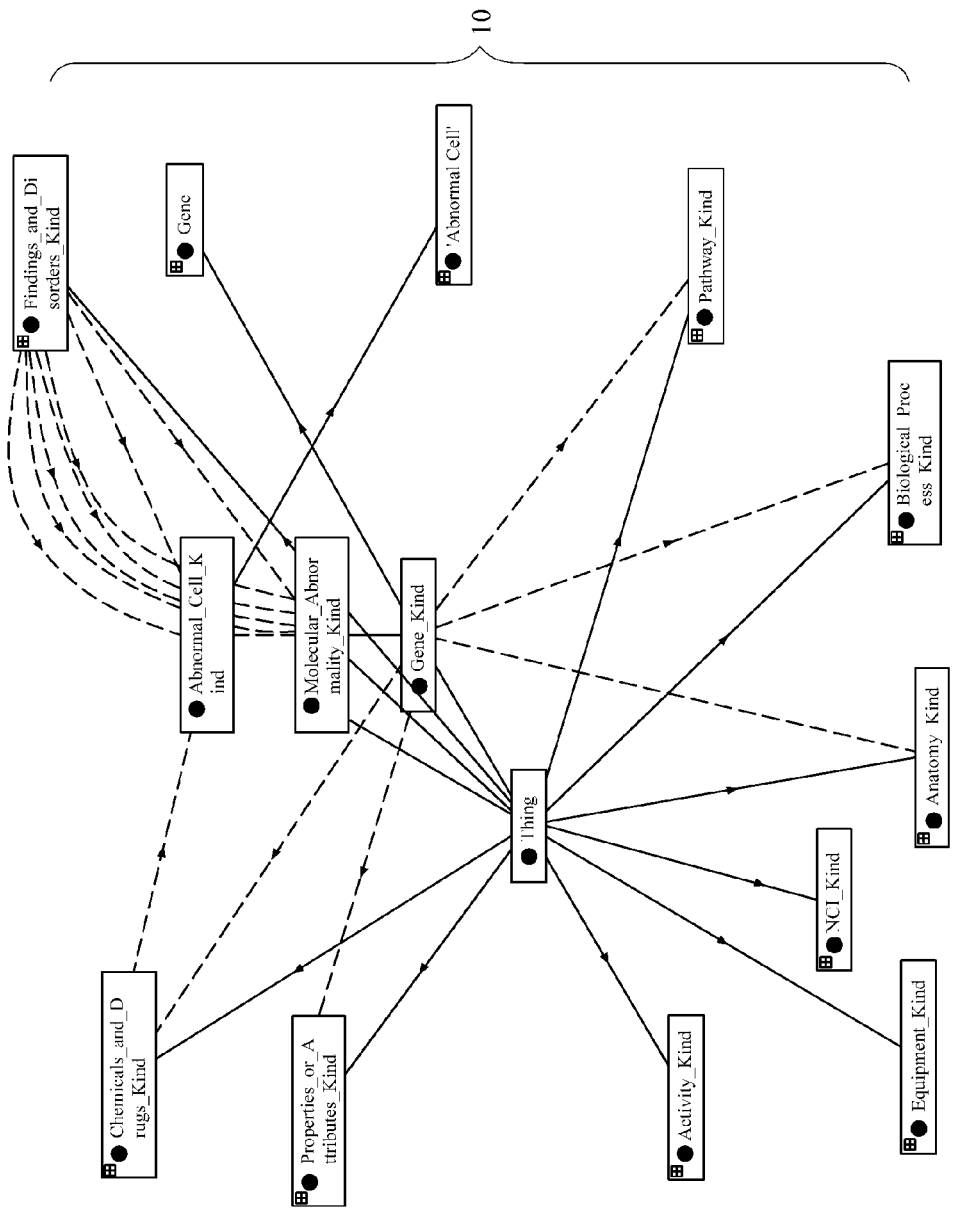
FIG. 1 is a diagram illustrating an embodiment of a biomedical ontology.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

FIG. 1 is a configuration diagram illustrating an embodiment of large-scale biomedical ontology according to the present invention.

Referring to FIG. 1, according to the present invention includes one or more components 10 of which mutual relations are established. The one or more components 10 establish relations between individual components 10 and corresponding components 10 via an ontology matching procedure, and matching results between these individual components 10 are collected to form ontology mapping. The ontology matching apparatus utilizes hardware of participating nodes in order to efficiently perform operations in the ontology matching procedure of the large-scale biomedical ontologies. The nodes participating in the distributed environment may include one or more nodes depending upon the available distributed environment. The ontology matching apparatus allocates ontology subsets to a multi-core processor provided in each one or more of the nodes and processes the ontology subsets by a data parallelization technique.

The biomedical ontology, like general ontology, belongs to a semantic-web ontology group. However, the biomedical ontology differs from general ontology in terms of size and evolution. The general ontology is smaller in size, and has a slower evolution than biomedical ontology. On the contrary, biomedical ontology evolves faster, and thus is greater in size by virtue of faster evolution in a biomedical domain and biomedical data.

The ontology matching in a distributed environment is a procedure in which a matching relation is set or connected based on a concept between source ontology and target ontology, which allows the classification system of ontologies to be expanded. The source ontology is ontology for establishing a new relation, and the target ontology is ontology to be matched with the source ontology via the ontology matching procedure.

The total number of matching operations between the source ontology and the target ontology is equally distributed over available operation resources (cores) as in Equation 1 below.

$$MT_{total} \leftarrow (m \times n) \forall\, m \in O_s, n \in O_t \quad \text{Equation 1}$$
$$MT_{core} \leftarrow \frac{m \times n}{numberofcores}$$

In Equation 1, $MT_{total}$ indicates the entire matching tasks, $O_S$ indicates the source ontology, $O_t$ indicates the target ontology, $MT_{core}$ indicates the matching task of the individual core, m indicates the concept of the source ontology, and n indicates the concept of the target ontology. Requests for the ontology matching of the large-scale biomedical ontologies may be generated from some sources including experts, researchers in biomedical fields, biomedical/bioinformatics systems, and even third-party healthcare information services performed on a cloud platform.

Figure 2:
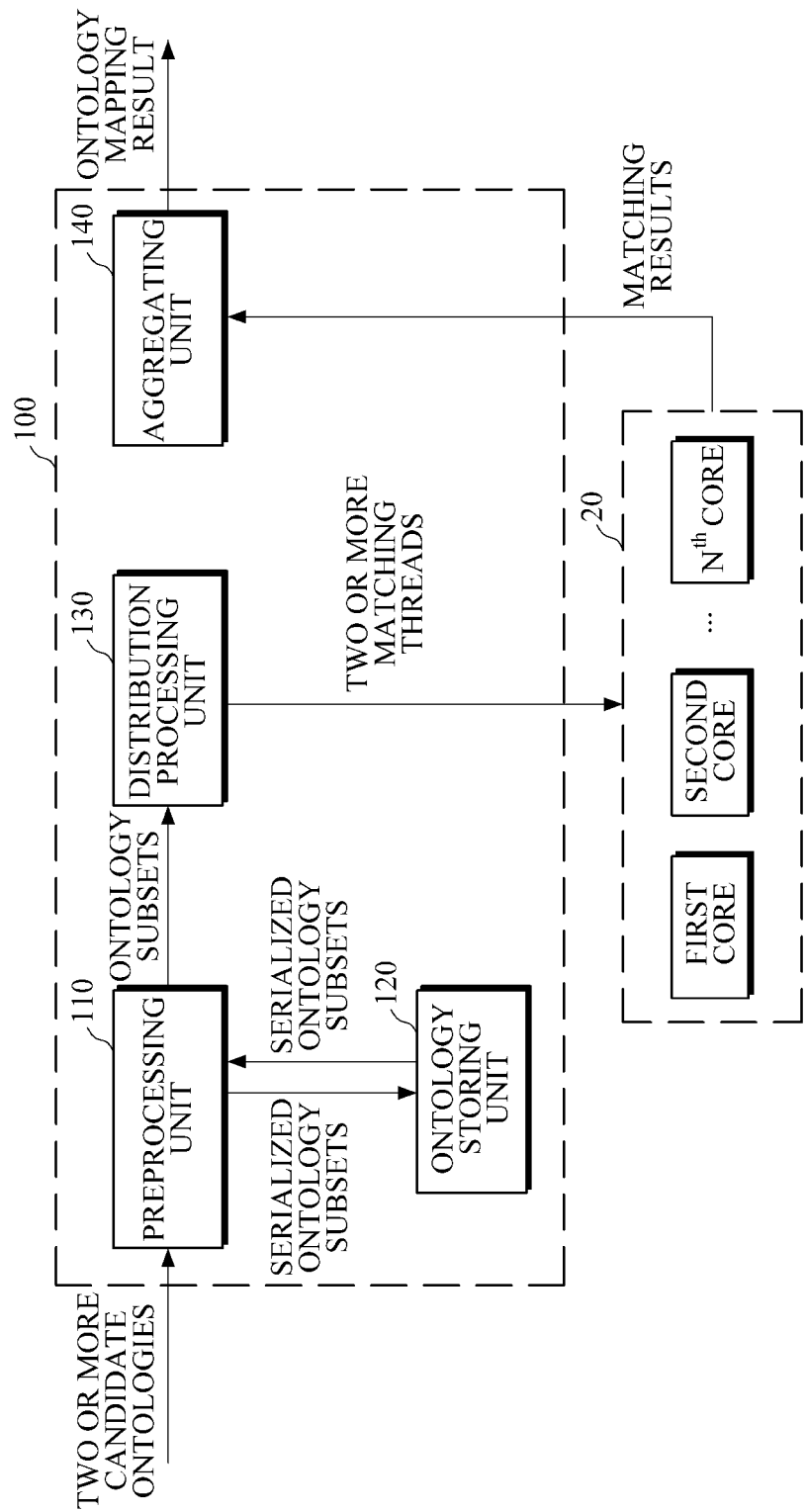
FIG. 2 is a configuration diagram illustrating an embodiment of an ontology matching apparatus for large-scale biomedical ontologies according to the present invention.

FIG. 2 is a configuration diagram illustrating an embodiment of the ontology matching apparatus of large-scale biomedical ontologies according to the present invention.

Referring to FIG. 2, the ontology matching apparatus 100 includes a preprocessing unit 110, an ontology storing unit 120, a distribution processing unit 130, and an aggregating unit 140.

The preprocessing unit 110 receives candidate ontologies, including source ontology and a target ontology. The candidate ontologies, including the source ontology and the target ontology, may match each other in one-to-one relation, one source ontology may match two or more target ontologies, or two or more source ontologies may match one target ontology.

The preprocessing unit 110 classifies the received candidate ontologies, including the source ontology and the target ontology, into one or more subsets. The ontology may generally consist of five subsets. The subsets constituting the ontology may generally be divided into name, label (this is misspelled in the Korean doc), relationship, axiom, and property. However, the ontology is not divided into only the five subsets described above, and the preprocessing unit 110 may classify the ontologies into one or more subsets in accordance with the kind or property of the received candidate ontologies regardless of the number of subsets. The preprocessing unit 110 delivers the classified ontology subsets to the ontology-storing unit 120 and the distribution processing unit 130. The preprocessing unit 110 may directly deliver the classified ontology subsets to the distribution processing unit 130, or may receive the ontology subsets that are already stored in the ontology storing unit 120, and then deliver them to the distribution processing unit 130. In particular, when the same candidate ontology as the ontology subset that is already classified and stored in the ontology storing unit 120 is received, the preprocessing unit 110 may deliver the ontology subset that is already serialized and stored in the ontology storing unit 120 to the distribution processing unit 130 without repeating the preprocessing procedure of classifying the ontologies into subsets, thereby reducing operation resources to be consumed in the preprocessing procedure. In addition, the preprocessing unit 110 may serialize the ontology subsets, and deliver them to the ontology storing unit 120, and may deserialize the serialized ontology subsets received from the ontology storing unit 120, and then deliver them to the distribution processing unit 130.

The ontology-storing unit 120 serializes the ontology subsets received from the preprocessing unit 110, and stores them. The ontology-storing unit 120 may serialize the received ontology subsets into a binary form to efficiently use a storage space, thereby increasing data processing efficiency. The ontology storing unit 120 may deliver the ontology subsets that are serialized into a binary form and stored in the ontology storing unit to the preprocessing unit 110 in accordance with a demand of the preprocessing unit 110, thereby avoiding or reducing unnecessary reprocessing in the preprocessing unit 110.

The distribution processing unit 130 divides the ontology subsets received from the preprocessing unit 110 into two or more matching threads for data parallelization. The data parallelization requires each processing core for performing a matching operation on each of the candidate ontologies divided into two or more distribution ontologies. To allow the parallelization processing to be performed, the distribution processing unit 130 divides the ontology subsets based on a distribution algorithm. The distribution processing unit 130 first confirms the number of cores of the multi-core processors of the individually participating nodes. The distribution processing unit 130 then applies the confirmed numbers of participating nodes and individually participating nodes to the distribution algorithm to divide the received ontology subsets into predetermined distribution ontologies.

The distribution processing unit 130 applies a matching library to one or more of the ontology subsets divided on the basis of the distribution algorithm to divide the ontology subsets into matching requests (hereinafter, referred to as MRs), matching jobs (hereinafter, referred to as MJs), and matching tasks (hereinafter, referred to as MTs). Equation 2 below denotes the relation among MR, MJ, and MT of the distribution algorithm applied to the distribution processing unit 130.

$$MR \leftarrow \sum_{i=1}^{Nodes} MR_i$$

$$MR_i \leftarrow \sum_{j=1}^{Cores} MJ_j$$

$$MJ_j \leftarrow \sum_{k=1}^{Copncepts} MT_k$$

$$MT_k \leftarrow m \times n \mid m \in O_s, n \in O_t$$

Equation 2

In equation 2, $MR_i$ indicates the MR received in each node, i indicates the number of participating nodes for parallel matching, MR indicates the MR received by the ontology matching apparatus 100 for matching, $MJ_j$ indicates the matching job allocated to the individual core 20 constituting each participating node, j indicates the number of individual cores 20 provided in the participating node, $MT_k$ indicates the MT that is allocated to one individual core 20 of each participating node and performs the matching operation, and k indicates the number of MTs included in the MJs allocated to one individual core 20. Further, m indicates the concept of the source ontology, and n indicates the concept of the target ontology. $Mt_k$, a single matching task, is a Cartesian product between concepts of the source and target ontologies.

The MR is a matching thread that corresponds and is delivered to each of the participating nodes (or CPUs of the participating nodes) constituting the distributed environment. The distribution processing unit 130 first divides the ontology subsets into one or more MRs corresponding to the respective participating nodes (or CPUs of the participating nodes) based on the number of participating nodes (or CPUs of the participating nodes). The maximum number of the MRs may be the number of the participating nodes (or CPUs of the participating nodes). That is, the MR may be the parallel processing job allocated to the individual node for ontology parallel processing. The distribution processing unit 130 divides the divided MRs into MJs again, and includes them in the corresponding MRs in accordance with the number of cores of the participating nodes to which the corresponding MRs are allocated. That is, the MJ is a parallel processing job allocated to the individual core 20, and the corresponding MR may include four MJs when the number of cores of the participating nodes to which the corresponding MRs are allocated is four. The distribution processing unit 130 then divides the MJs to be allocated to the individual cores into MTs that are units for actually performing the matching processing, and includes them in the MJs.

The MR, the MJ, and the MT are three layers of abstraction for the entire matching process. Since the distribution algorithm for the parallel processing needs to provide classification of different levels, the distribution algorithm of the distribution processing unit 130 needs to preserve all running job tracks.

The MT is a unit of the matching process and may be classified as the smallest unit for the entire matching processes. For example, when the source ontologies are {A, B, C, D} and the target ontologies are {a, b, c, d} in the MJs allocated to the core of the corresponding participating node, A=a may be the first MT, B=b may be the second MT, C=c may be the third MT, and D=d may be the fourth MT during the matching process by comparing the source ontologies with the target ontologies. When A=d may be compared and matched with each other, A=d may be another MT. That is, the MT is the smallest unit by which the individual matching process is processed within the individual core of the participating node, and processes the matching processing of individual terms constituting the ontology within the core.

The MJ is a unit allocated to each core 20 of the participating node, and by which the matching process is performed, and may be a collection of one or more MTs. The MR is a collection of all MJs performed in one participating node (or CPU of the participating node).

For example, when four nodes are participating in the matching process, and each has four cores, and the received ontology subsets require 2000 matchings in total, the distribution processing unit 130 divides the 2000 matchings by four into four MRs in accordance with the number of the participating nodes. Each of the four divided MRs includes 500 matchings. The distribution processing unit 130 classifies each of the four MRs into four MJs based on the number of cores. Each of the MJs then includes 125 matchings that are obtained by dividing 500 matchings by four. As a result, one MJ includes 125 matchings, and the number of MTs included in the individual MJ is 125. That is, each of the four MRs includes four MJs, each of the four MJs includes 125 MTs, and one or more ontology subsets, including 2000 matchings in total, are thus divided into four MRs, each of the MRs includes four MJs, and each of the MJs includes 125 MTs.

The numbers of MRs, MJs, and MTs may be set in consideration of not only the participating nodes and the number of the individually participating nodes, but also a scenario in which the most optimized parallel processing can be performed. Each MJ itself is independent of other MJs and other remotely operating MRs. In addition, when the number of the MTs included in one or more MJs is kept the same among one or more MJs in the procedure of subdividing the MRs into the MJs, most individual cores can terminate the matching operation at a similar time to generate the matching results, thereby preventing available matching cores from being idle. The MR, the MJ, and the MT will be described later with reference to FIG. 5.

The distribution processing unit 130 delivers a predetermined number of MRs included in one or more ontology subsets to the participating nodes as described above. One of the MRs is delivered to the corresponding one of the participating nodes. The one MR delivered to the one participating node of the nodes includes MJs corresponding to respective one or more cores included in the corresponding participating node. The one or more MJs included in one MR are allocated to the corresponding cores in one-to-one relation. One MJ allocated to one core performs the matching processing on the corresponding core via the included MTs. Accordingly, the ontology matching apparatus 100 for large-scale biomedical ontologies according to the present invention may perform parallelization processing on each of the cores of the participating nodes.

The aggregating unit 140 receives matching results in which the matching operations are performed via the matching threads from the individual cores 20 of the participating nodes that received the matching threads from the distribution processing unit 130. The distribution processing unit 130 delivers the matching threads, including the MRs, the MJs, and the MTs, to respective cores of the participating nodes. The individual cores 20 of the participating nodes that received the matching threads, including the MRs, the MJs, and the MTs from the distribution processing unit 130 perform the matching operations based on the received matching threads. The participating nodes that received the MRs included in the matching threads allocates the MJs to the individual cores 20 in accordance with the MJs included in the MRs, and the individual cores 20 perform the MTs included in the allocated MJs, thereby carrying out the matching processing of the received candidate ontologies in parallel. The aggregating unit 140 collects the matching results (operation results) generated by the ontology matching operations performed in the individual cores.

The aggregating unit 140 may directly receive the matching results generated in the individual cores 20 from the individual cores 20, or may receive the matching results generated in the individual cores 20 from the participating node including the individual cores 20 at one time.

The aggregating unit 140 aggregates the matching results received from the individual cores 20 to generate ontology mapping. The ontology mapping is a collection of individual matching results among components of two or more candidate ontologies. The aggregating unit 140 accumulates the matching results operated by operations of the MJs, and applies a bridge pattern to the accumulated matching results to generate a formal representation of the ontology mapping. The bridge pattern is a kind of mapping file, and is a custom-defined format for mapping files depending on individual users. For example, when a mapping file in the XML format is desired along with a specific schema, the format may be different from a mapping format defined by another user. All such individual formats are referred to as the bridge pattern. That is, the aggregating unit 140 may provide ontology mapping to be consistent with the individual format desired by the individual user by virtue of the bridge pattern. The aggregating unit 140 stores the used bridge pattern for another user.

The aggregating unit 140 may have a different summation procedure in accordance with the number of participating nodes.

$$O_b^{Job} \leftarrow \bigcup_{i=1}^{MT} O_b^i \qquad \text{Equation 3}$$

$$O_b^{Node} \leftarrow \sum_{i=0}^{MJ} O_b^{job=i}$$

$$O_b \leftarrow \sum_{i=1}^{TotalNode} O_b^{Node=i}$$

Equation 3 indicates three operations for generating a bridge ontology in the distributed environment to which two or more participating nodes are connected. The first operation collects all results of single MTs in all MJs. In the first operation, $O_b^i$ indicates the matching result of the MT (bridge ontology of the MT), and $O_b^{Job}$ indicates an intermediate bridge ontology of the MJ. The second operation sums results of all MJs performed in one participating node. In the second operation, $O_b^{Node}$ indicates a sum of all intermediate bridge ontologies $O_b^{Job}$ in all MJs performed in each of the participating nodes. The intermediate bridge ontologies $O_b^{Job}$ generated in all of the current nodes become intermediate bridge ontologies from the nodes. The third operation sums all matching results of all MRs performed in all nodes participating in a distributed environment. In the third operation, $O_b$ indicates the finally generated bridge ontology, and $O_b$ is converted to an ontology mapping result as an output file.

$$O_b^{Job} \leftarrow \bigcup_{i=1}^{MT} O_b^i \qquad \text{Equation 4}$$

$$O_b^{Node} \leftarrow \sum_{i=0}^{MJ} O_b^{job=i}$$

Equation 4 indicates two operations for generating the bridge ontology in the distributed environment to which one participating node is connected. When the number of participating node is one, results of the MJs performed in the individual cores 20 of the single participating node CPU need to be summed. The first operation incorporates results $O_b^i$ of all MTs performed in the single MJ, and the incorporated result of the MT results $O_b^i$ is the intermediate bridge ontology $O_b^{Job}$ of MJs. The second operation sums results of all MJs performed in one participating node. The sum of all intermediate bridge ontologies $O_b^{Job}$ in the MJs performed in the single participating node becomes the intermediate bridge ontologies $O_b^{Node}$ from the node.

The matching results operated by all nodes participating in the distributed environment are summed as one ontology object referred to as bridge ontology. The aggregating unit 140 converts the collected bridge ontology to an ontology mapping result as a physical mapping file and outputs the ontology mapping result.

Figure 3:
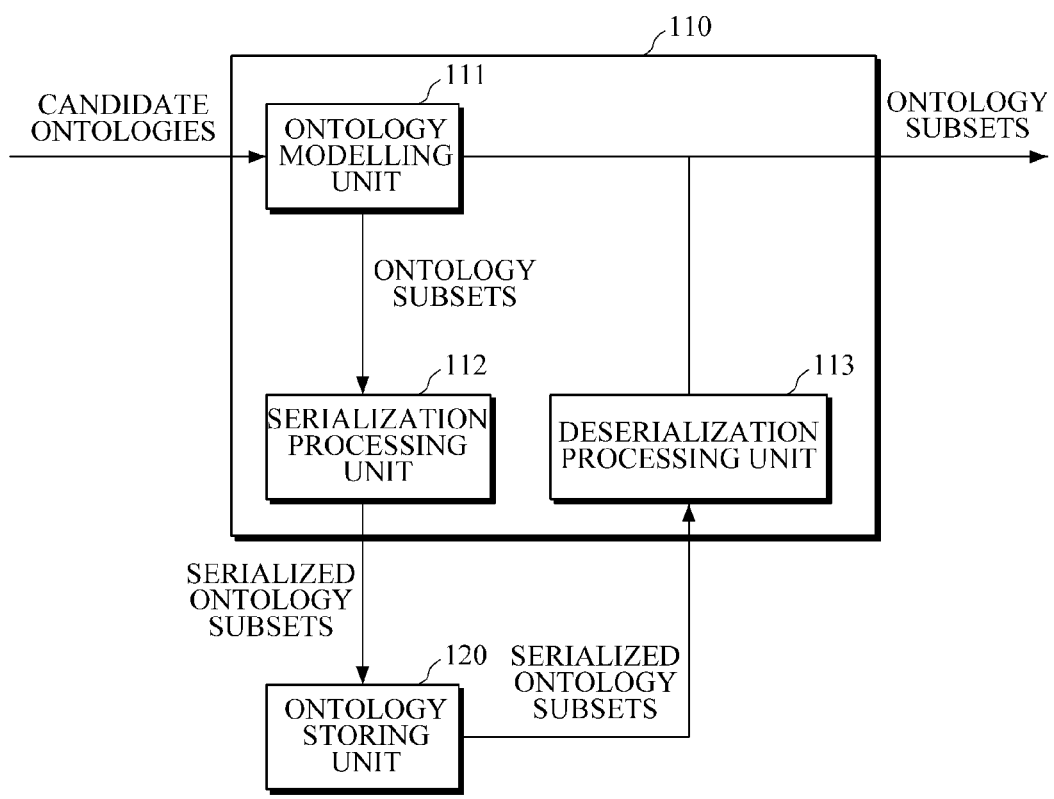
FIG. 3 is a detailed diagram illustrating a preprocessing unit of an ontology matching apparatus for large-scale biomedical ontologies according to an embodiment of the present invention.

FIG. 3 is a detailed diagram illustrating the preprocessing unit of the ontology matching apparatus for large-scale biomedical ontologies according to an embodiment of the present invention.

Referring to FIG. 3, the preprocessing unit 110 of the ontology matching apparatus 100 for the large-scale biomedical ontologies according to an embodiment of the present invention includes an ontology modeling unit 111, a serialization processing unit 112, and a deserialization processing unit 113.

The ontology modeling unit 111 receives candidate ontologies including a source ontology and a target ontology. The candidate ontologies including the source ontology and the target ontology match each other in one-to-one relation, one source ontology may match two or more target ontologies, or two or more source ontologies may match one target ontology.

The ontology modeling unit 111 classifies the received candidate ontologies including the source ontology and the target ontology into one or more subsets. The ontologies may generally consist of five subsets. The subsets constituting the ontology may be generally divided into name, label, relationship, axiom, and property. However, the ontology is not divided into only the five subsets described above, and the ontology modeling unit 111 may classify the candidate ontologies into one or more subsets in accordance with the kind or property of the received candidate ontologies regardless of the number of subsets. In addition, the ontology modeling unit 111 may classify the candidate ontologies into one or more subsets in consideration of matching libraries including the matching algorithm. The ontology modeling unit 111 delivers the classified ontology subsets to the distribution processing unit 130.

The serialization processing unit 112 serializes the ontology subsets generated in the ontology modeling unit 111. The serialization processing unit 112 may serialize the ontology subsets that are classified into two or more subsets into a binary form to efficiently use the storage space, thereby increasing the data transmitting and processing efficiency. The serialization processing unit 112 may deliver the serialized ontology subsets to the ontology storing unit 120 for storage. The ontology storing unit 120 may store the serialized ontology subsets to efficiently use the storage space, thereby increasing the data processing efficiency.

The deserialization processing unit 113 reconfigures the serialized ontology subsets that are stored in the ontology storing unit 120 in the form serialized by the serialization processing unit 112, to the original ontology subsets. Accordingly, the ontology subsets that are serialized into the binary form and stored in the ontology storing unit 120 are delivered to the deserialization processing unit 113 in accordance with the demand of the ontology modeling unit 111, thereby avoiding or reducing the unnecessary reprocessing in the ontology modeling unit 111. That is, when the same candidate ontology as the ontology subset that is already classified and stored in the ontology storing unit 120 is received, the preprocessing procedure of classifying the ontologies into subsets does not need to be repeated, and the ontology subsets serialized and stored in the ontology storing unit 120 may be directly restored (reconfigured) by the deserialization processing unit 113 and then delivered to the distribution processing unit 130. This allows the preprocessing to be skipped, thereby reducing the operation resources to be consumed in the preprocessing.

The preprocessing procedure of the preprocessing unit 110 subdividing the received candidate ontologies into subsets and generating the subset ontologies allows lesser memory footprints to be implemented for the running time.

Figure 4:
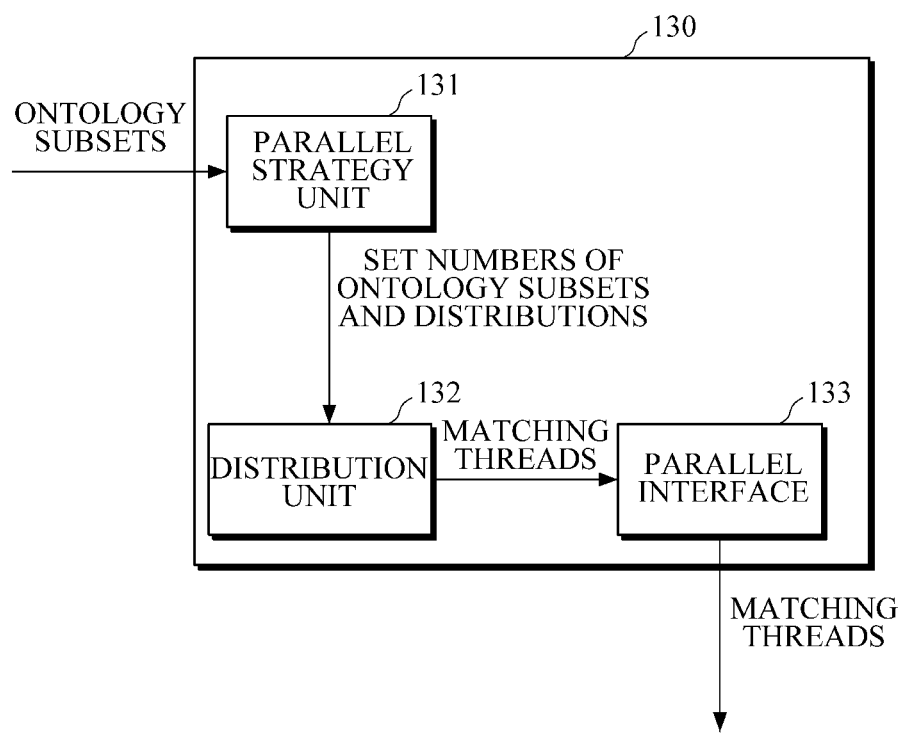
FIG. 4 is a detailed diagram illustrating a distribution processing unit of an ontology matching apparatus for large-scale biomedical ontologies according to an embodiment of the present invention.

FIG. 4 is a detailed diagram illustrating the distribution processing unit of the ontology matching apparatus for large-scale biomedical ontologies according to an embodiment of the present invention.

Referring to FIG. 4, the distribution processing unit 130 of the ontology matching apparatus for the large-scale biomedical ontologies according to an embodiment of the present invention includes a parallel strategy unit 131, a distribution unit 132, and a parallel interface 133.

The parallel strategy unit 131 confirms the number of participating nodes and the number of individual cores (multi cores) provided in each of the participating nodes. The distributed environment includes a large number of nodes participating via a network. The participating nodes may include not only generally used personal computers such as desktops and notebooks but also terminals or apparatuses capable of performing operations such as workstations and server computers. The ontology matching apparatus for large-scale biomedical ontologies according to the present invention distributes the ontology matching for matching the candidate ontologies into the individual cores of the participating nodes and performs parallel processing. Thus, the parallel strategy unit 131 confirms the number of participating nodes and the number of individual cores provided in each of the participating nodes to find out available operation resources. The parallel strategy unit 131 then sets the optimal number of distributions based on the distribution algorithm and the confirmed numbers of the participating nodes and individual cores.

The distribution unit 132 divides the ontology subsets in consideration of the optimal number of distributions set based on the distribution algorithm and the confirmed numbers of the participating nodes and individual cores, and applies the matching algorithm of the matching library to the divided ontology subsets to generate matching threads. The generated matching threads include MRs, MJs, and MTs. The matching algorithm stored in the matching library is an algorithm for operating matching among individual components constituting the candidate ontologies in order to generate the ontology mapping among the candidate ontologies, and may include matching algorithms that may be applied to the ontology matching such as synonym-based matching, label-based matching, broader term-based matching, and child-based matching.

The MR generated in the distribution unit 132 is a matching thread that corresponds to and is delivered to each of the participating nodes (or CPUs of the participating nodes). The parallel strategy unit 131 first divides the ontology subsets into one or more MRs corresponding to the respective participating nodes (or CPUs of the participating nodes) in consideration of the number of participating nodes (or CPUs of the participating nodes). The maximum number of the MRs may be the number of the participating nodes (or CPUs of the participating nodes). That is, MR may be the parallel processing job allocated to the individual node for ontology parallel processing. The distribution unit 132 divides the divided MRs into MJs again and includes them in the corresponding MRs in accordance with the number of cores of the participating nodes to which the corresponding MRs are allocated. That is, the MJ is a parallel processing job allocated to the individual core, and the corresponding MR may include four MJs when the number of cores of the participating nodes to which the corresponding MRs are allocated is four. The distribution unit 132 then divides the MJs to be allocated to the individual cores into MTs that are units for actually performing the matching processing and then includes them in the MJs.

The MR, the MJ, and the MT are three layers of abstraction for the entire matching process. Since the distribution algorithm for the parallel processing needs to provide classification of different levels, the distribution algorithm of the distribution unit 132 needs to preserve all running job tracks.

The MT is a unit of the matching process and may be classified as the smallest unit for entire matching processes. For example, when the source ontologies are {A, B, C, D} and the target ontologies are {a, b, c, d} in the MJs allocated to the core of the corresponding participating node, A=a may be the first MT, B=b may be the second MT, C=c may be the third MT, and D=d may be the fourth MT during the matching process by comparing the source ontologies with the target ontologies. When A=d may be compared and matched with each other, A=d may be another MT. That is, the MT is the smallest unit by which the individual matching processing is processed within the individual cores of the participating node, and processes the matching processing of individual terms constituting the ontology within the core.

The MJ is a unit allocated to the individual core of the participating node and by which the matching process is performed, and may be a collection of one or more MTs. The MR is a collection of all MJs performed in one participating node (or CPU of the participating node).

For example, when four nodes are participating and each have four cores and the received ontology subsets require 2000 matchings in total, the distribution unit 132 divides the 2000 matchings by four into four MRs in accordance with the number of the participating nodes. Each of the four divided MRs includes 500 matchings. The distribution unit 132 classifies each of the four MRs into four MJs based on the number of cores. Each of the MJs then includes 125 matchings that are obtained by dividing 500 matchings by four. As a result, one MJ includes 125 matchings, and the number of MTs included in the individual MJ is 125. That is, each of the four MRs includes four MJs, each of the four MJs includes 125 MTs, and one or more ontology subsets including 2000 matchings in total are thus divided into four MRs, each of the MRs includes four MJs, and each of the MJs includes 125 MTs. The numbers of MR, MJ, and MT may be set in consideration of not only the participating nodes and the number of the individually participating nodes but also the scenario in which the most optimized parallel processing can be performed. Each MJ itself is independent of other MJs and other remotely operating MRs.

The parallel interface 133 delivers the matching threads to the participating nodes and individual cores of each participating node. One MR is delivered to the corresponding one participating node. The one MR delivered to the one participating node includes MJs corresponding to the respective one or more cores included in the corresponding participating node. The one or more MJs included in the one MR are allocated to the corresponding cores in one-to-one relation. One MJ allocated to one core performs the matching processing on the corresponding core via the included MT. Accordingly, the ontology matching apparatus for large-scale biomedical ontologies according to the present invention may perform parallelization processing in each of the cores of the participating nodes.

Figure 5:
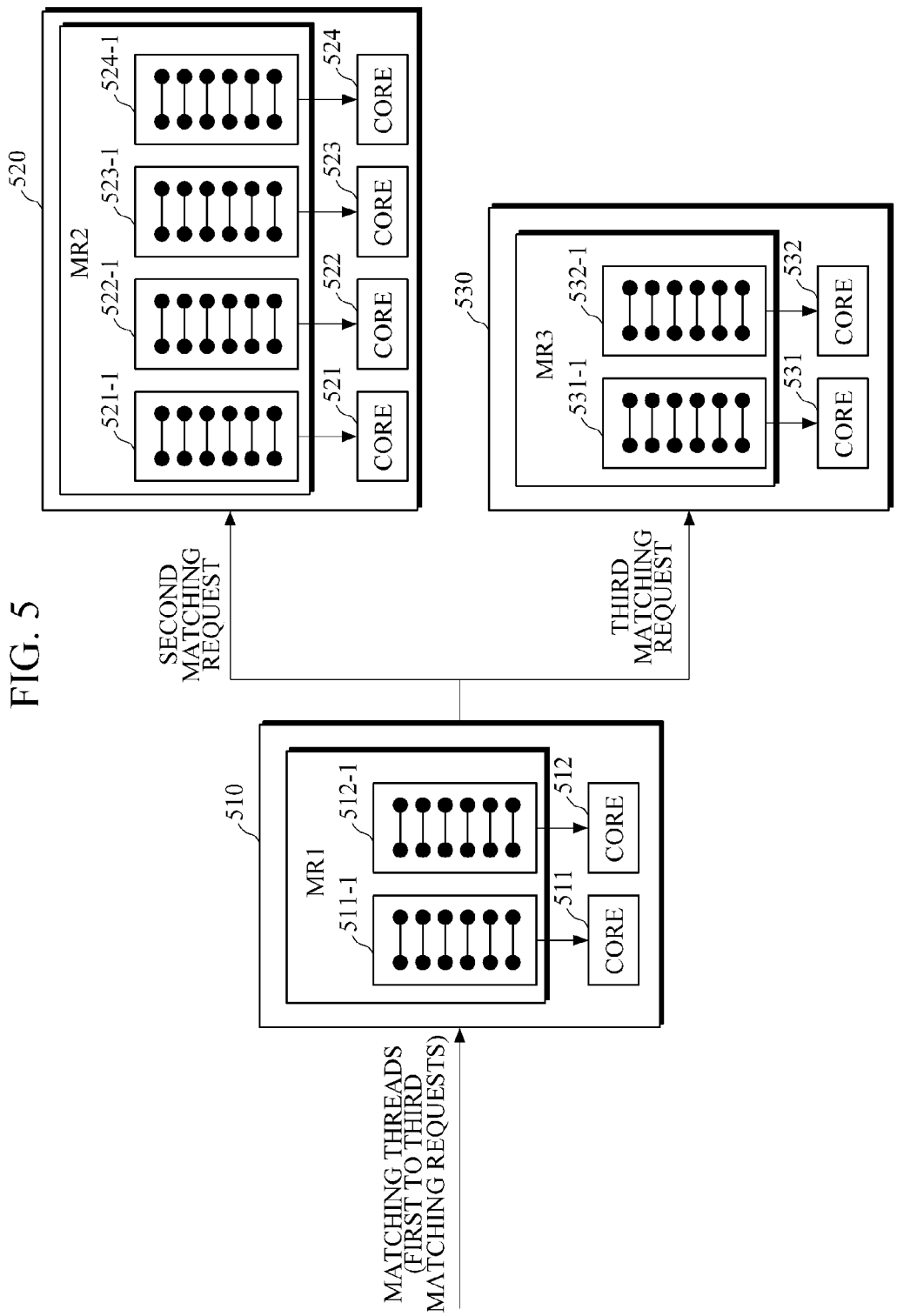
FIG. 5 is a diagram illustrating an embodiment of matching threads delivered to individual cores in an ontology matching apparatus in a distributed environment according to an embodiment of the present invention.

FIG. 5 is a diagram illustrating an embodiment of matching threads delivered to individual cores in the ontology matching apparatus for large-scale biomedical ontologies according to an embodiment of the present invention.

Referring to FIG. 5, the matching threads generated in the distribution processing unit of the ontology matching apparatus for large-scale biomedical ontologies according to the present invention may include MRs, MJs, and MTs corresponding to the respective nodes and respective individual nodes. For example, it is assumed that three participating nodes including a first node 510, a second node 520, and a third node 530 are connected in a distributed environment. The first node 510 includes two cores 511 and 512, the second node 520 includes four cores 521, 522, 523, 524, and the third node 530 includes two cores 531 and 532. The ontology matching apparatus generates two or more matching threads by virtue of the preprocessing and distribution processing procedures from the candidate ontologies including the source ontology and the target ontology, and delivers the generated two or more matching threads to the individual cores of each participating node.

The MR is a matching thread that corresponds to and is delivered to each of the participating nodes (or CPUs of the participating nodes). The distribution processing unit 130 first divides the ontology subsets into one or more MRs corresponding to the respective participating nodes (or CPUs of the participating nodes) in consideration of the number of participating nodes (or CPUs of the participating nodes). The maximum number of the MRs may be the number of the participating nodes (or CPUs of the participating nodes). That is, MR may be the parallel processing job allocated to the individual node for ontology parallel processing. The ontology matching apparatus for large-scale biomedical ontologies divides the divided MRs into MJs again and includes them in the corresponding MRs in accordance with the number of cores of the participating nodes to which the corresponding MRs are allocated. That is, the MJ is a parallel processing job allocated to the individual core, and the corresponding MR may include four MJs when the number of cores of the participating nodes to which the corresponding MRs are allocated is four. The distribution processing unit 130 then divides the MJs to be allocated to the individual cores into MTs that are units for actually performing the matching processing and includes them in the MJs.

In FIG. 5, three nodes 510, 520, and 530 are included in total, and the ontology matching apparatus for large-scale biomedical ontologies classifies the candidate ontologies into subsets and applies the distribution and matching algorithms to the subsets to generate matching threads including three MRs MR1, MR2, and MR3. The first MR MR1 corresponds to the first node 510, the second MR MR2 corresponds to the second node 520, and the third MR MR3 corresponds to the third node 530. The first MR MR1 includes two MJs 511-1 and 512-1 corresponding to two cores 511 and 512 provided in the first node 510, the second MR MR2 includes four MJs 521-1, 522-1, 523-1, and 524-1 corresponding to four cores 521, 522, 523, and 524 provided in the second node 520, and the third MR MR3 includes two MJs 531-1 and 532-1 corresponding to two cores 531 and 532 provided in the third node 530.

The first to third MRs MR1, MR2, and MR3 and the MJs included in the MRs 511-1, 512-1, 521-1, 522-1, 523-1, 524-1, 531-1, and 532-1 are generated so as to correspond to the participating nodes 510, 520, and 530 connected in a distributed environment and the individual cores of the respective participating nodes 511, 512, 521, 522, 523, 524, 531, and 532. The generated first to third MRs MR1, MR2, and MR3 are delivered to the first node 510, the second node 520, and the third node 530, respectively. The procedure of delivering the MR to each node in the ontology matching apparatus for the large-scale biomedical ontologies may directly deliver the MR to each node from the ontology matching apparatus for the large-scale biomedical ontologies, or may deliver the MR to one node from the ontology matching apparatus for the large-scale biomedical ontologies and then sequentially deliver the MR to the connected nodes in accordance with the structure of the distributed environment.

Figure 6:
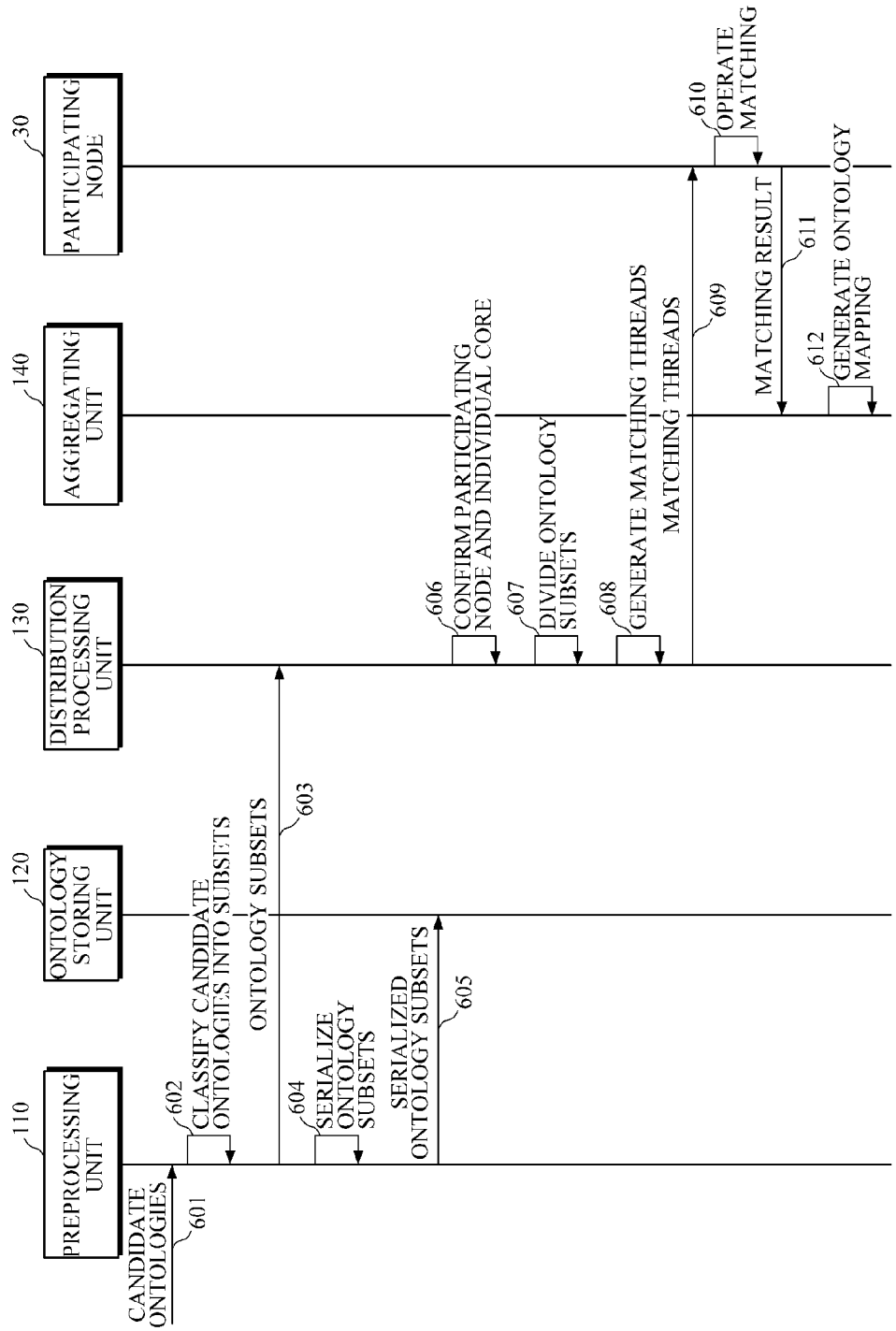
FIG. 6 is a diagram illustrating a data flow of an ontology matching apparatus for large-scale biomedical ontologies according to an embodiment of the present invention.

FIG. 6 is a diagram illustrating a data flow of the ontology matching apparatus for the large-scale biomedical ontologies according to an embodiment of the present invention.

Referring to FIG. 6, the preprocessing unit 110 first receives candidate ontologies including a source ontology and a target ontology in the data flow of the ontology matching apparatus for the large-scale biomedical ontologies according to an embodiment of the present invention (601). The candidate ontologies including the source ontology and the target ontology may match each other in one-to-one relation, one source ontology may match two or more target ontologies, or two or more source ontologies may match one target ontology.

The preprocessing unit 110 classifies the received candidate ontologies including the source ontology and the target ontology into one or more subsets (602). The ontology may generally consist of five subsets. The subsets constituting the ontology may be generally divided into name, label, relationship, axiom, and property. However, the ontology is not divided into only the five subsets described above, and the preprocessing unit 110 may classify the candidate ontologies into one or more subsets in accordance with the kind or property of the received candidate ontologies regardless of the number of subsets. The preprocessing unit 110 delivers the classified ontology subsets to the distribution processing unit 130 (603).

Next, the preprocessing unit 110 serializes the classified ontology subsets (604). The preprocessing unit 110 may serialize the received ontology subsets into a binary form to increase the data processing efficiency and the storage space efficiency. The preprocessing unit 110 delivers the serialized ontology subsets to the ontology storing unit 120 for storage (605). Afterwards, when the same candidate ontology is received, the corresponding ontology subsets stored in the ontology storing unit 120 are invoked and used. Accordingly, the preprocessing procedure of classifying the ontologies into subsets may be omitted to save time and operation resources.

When the ontology subsets are delivered from the preprocessing unit 110 to the distribution processing unit 130 (603), the distribution processing unit 130 confirms the number of participating nodes 30 and the number of individual cores of each of the participating nodes 30 (606). The distribution processing unit 130 first confirms the number of the participating nodes 30 and the number of individual cores provided in each of the participating nodes to find out available operation resources. The distribution processing unit 130 sets the optimal number of distributions based on the distribution algorithm and the confirmed numbers of the participating nodes 30 and the individual cores.

The distribution processing unit 130 divides the ontology subsets in consideration of the set optimal number of distribution based on the distribution algorithm and the confirmed numbers of the participating nodes 30 and the individual cores (607), and applies the matching algorithm of the matching library to the divided ontology subsets to generate matching threads (608). The generated matching threads include MRs, MJs, and MTs. The matching algorithm stored in the matching library is an algorithm for operating matching among individual components constituting the candidate ontologies in order to generate the ontology mapping among the candidate ontologies, and may include matching algorithms that may be applied to the ontology matching such as synonym-based matching, label-based matching, broader term-based matching, and child-based matching.

The distribution processing unit 130 first divides the ontology subsets into one or more MRs corresponding to the respective participating nodes 30 in consideration of the number of participating nodes 30. The maximum number of the MRs may be the number of the participating nodes 30. The distribution processing unit 130 then divides the divided MRs into MJs again and includes them in the corresponding MRs in accordance with the number of cores of the participating nodes 30 to which the corresponding MRs are allocated. The MR, the MJ, and the MT are three layers of abstraction for the entire matching process. Since the distribution algorithm for the parallel processing needs to provide classification of different levels, the distribution algorithm of the distribution unit 132 needs to preserve all running job tracks. The numbers of MR, MJ, and MT may be set in consideration of not only the participating nodes 30 and the number of the individually participating nodes 30 but also the scenario in which the most optimized parallel processing can be performed. Each MJ itself is independent of other MJs and other remotely operating MRs.

The distribution processing unit 130 that has generated the matching threads delivers the generated matching threads to the corresponding participating nodes 30, respectively (609). The nodes that have received the corresponding matching threads from the distribution processing unit 130 allocate the MJs included in the MRs of the received matching threads to individual nodes, respectively. One MR is delivered to the corresponding one participating node 30. The one MR delivered to the one participating node 30 includes MJs corresponding to the respective one or more cores included in the corresponding participating node 30. The one or more MJs included in the one MR are allocated to the corresponding cores in one-to-one relation.

The individual cores of the participating node 30 to which the MJ included in the matching thread is allocated by the participating node 30 perform the matching operation based on the MTs included in the MJs (610). The MJ allocated to the individual core includes one or more MTs. The MTs includes the matching algorithm for performing the matching operation of the components constituting the candidate ontologies, and divided and subdivided ontology subsets. The individual cores perform the ontology matching operation based on the MTs. The participating node 30 delivers the matching result generated by the matching operation performed in the individual core to the aggregating unit 140 (611). The aggregating unit 140 receives the matching result in which the matching operation is performed by matching threads from the participating node that has received the matching threads from the distribution processing unit 130. The aggregating unit 140 then aggregates the matching results received from the participating nodes 30 to generate the ontology mapping (612). The ontology mapping is a collection of individual matching results among components of two or more candidate ontologies. The aggregating unit 140 accumulates the matching results operated by operations of the MJs in the individual cores, and applies a bridge pattern to the accumulated matching results to generate a formal representation of the ontology mapping. The bridge pattern is a kind of mapping file, and is a custom-defined format for mapping files depending on individual users. That is, the aggregating unit 140 may provide the ontology mapping to be consistent with the individual format desired by the individual user by virtue of the bridge pattern. The aggregating unit 140 stores the used bridge pattern for another user.

Figure 7:
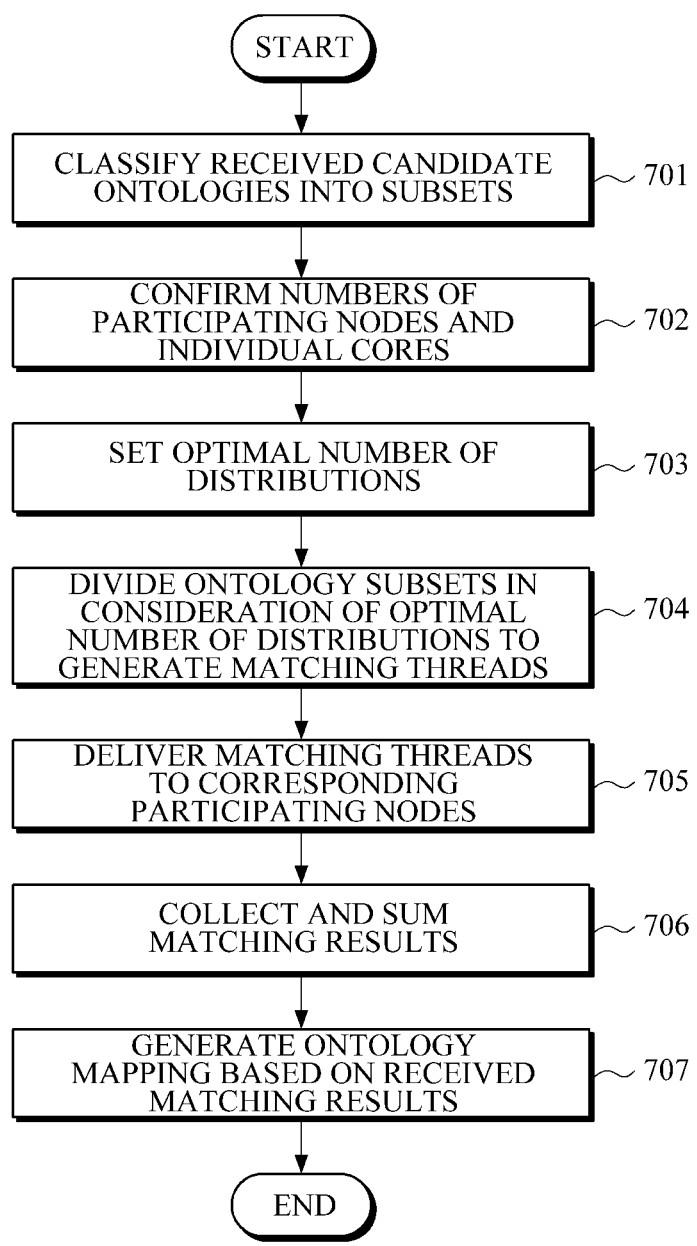
FIG. 7 is a flowchart illustrating an ontology matching method for large-scale biomedical ontologies according to an embodiment of the present invention.

FIG. 7 is a flowchart illustrating the ontology matching method for the large-scale biomedical ontologies according to an embodiment of the present invention.

Referring to FIG. 7, the ontology matching method for the large-scale biomedical ontologies according to an embodiment of the present invention first classifies candidate ontologies including a source ontology and a target ontology into one or more subsets (701). The ontology may generally consist of five subsets. The subsets constituting the ontology may be generally divided into name, label, relationship, axiom, and property. However, the ontology is not divided into only the five subsets described above, and may be classified into one or more subsets in accordance with the kind or property of the received candidate ontologies regardless of the number of subsets.

When the candidate ontologies are classified into one or more subsets, the number of participating nodes and the number of individual cores provided in each of the participating nodes are confirmed (702). The ontology matching apparatus for the large-scale biomedical ontologies first confirms the number of the participating nodes and the number of individual cores provided in each of the participating nodes to find out available operation resources. The ontology matching apparatus for the large-scale biomedical ontologies then sets the optimal number of distributions in consideration of the distribution algorithm and the confirmed numbers of the participating nodes and the individual cores (703).

When the numbers of the participating nodes and the individual cores are applied to the distribution algorithm to set the optimal number of distributions, the ontology subsets are divided in consideration of the set optimal number of distributions, and the matching algorithm of the matching library is applied to the divided ontology subsets to generate the matching threads (704). The generated matching threads include MRs, MJs, and MTs. The matching algorithm stored in the matching library is an algorithm for operating matching among individual components constituting the candidate ontologies in order to generate the ontology mapping among the candidate ontologies. The ontology matching apparatus for the large-scale biomedical ontologies first divides the ontology subsets into one or more MRs corresponding to the respective participating nodes in consideration of the number of participating nodes. The ontology matching apparatus for the large-scale biomedical ontologies then divides the divided MRs into MJs again and includes them in the corresponding MRs in accordance with the number of cores of the participating nodes to which the corresponding MRs are allocated.

When the matching threads are generated, the generated matching threads are delivered to the corresponding participating nodes (705). The individual cores of the participating nodes to which the MJs included in the matching threads are allocated perform the matching operation based on the MTs included in the MJs.

When the matching operation based on the matching threads is performed in the individual cores of the participating nodes, matching results from the matching operation are collected and summed (706). The ontology matching apparatus for the large-scale biomedical ontologies collects the matching results generated by virtue of the matching operation performed in the individual cores of the participating nodes, and sums the collected matching results to generate the ontology mapping (707). The ontology mapping is a collection of individual matching results among components of two or more candidate ontologies. The ontology matching apparatus for the large-scale biomedical ontologies accumulates the matching results operated by operations of the MJs in the individual cores of the participating nodes, and applies a bridge pattern to the accumulated matching result to generate a formal representation of the ontology mapping.

Figure 8:
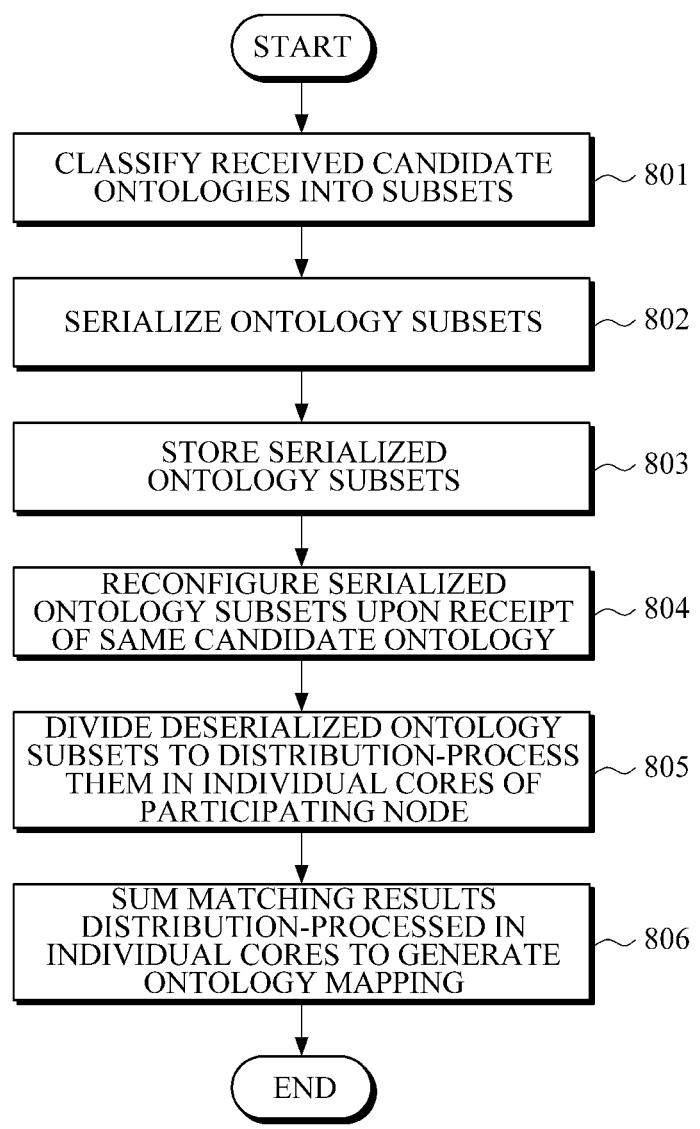
FIG. 8 is a flowchart illustrating a preprocessing omission method of an ontology matching method for large-scale biomedical ontologies according to an embodiment of the present invention.

FIG. 8 is a flowchart illustrating the preprocessing omission method of the ontology matching method for the large-scale biomedical ontologies according to an embodiment of the present invention.

Referring to FIG. 8, in order to omit the preprocessing procedure, the ontology matching method for the large-scale biomedical ontologies according to an embodiment of the present invention first classifies received candidate ontologies into subsets (801). The ontologies may generally consist of five subsets. The subsets constituting the ontologies may be generally divided into name, label, relationship, axiom, and property.

When the candidate ontologies are classified into ontology subsets, the classified ontology subsets are serialized (802). The ontology subsets classified into two or more subsets may be serialized in a binary form to efficiently use the storage space and increase the data transfer and processing efficiency. And the serialized ontology subsets are stored (803). Since the ontology subsets are serialized and stored, the storage space can be efficiently used and the data processing efficiency can be increased.

Afterwards, when the same candidate ontology as the already received candidate ontology is received, the serialized ontology subsets stored in the serialized form are reconfigured to be the original ontology subsets (804). By deserializing the serialized and stored ontology subsets again as described above, reprocessing the unnecessary preprocessing can be reduced or avoided. That is, when the same candidate ontology as the already received candidate ontology is received, the preprocessing procedure of classifying the candidate ontologies into subsets is not repeated and the serialized ontology subsets are restored (reconfigured) by deserialization to omit the preprocessing procedure, thereby reducing the operation resources to be consumed in the preprocessing procedure.

The ontology subsets reconfigured by the deserialization are divided to be distributed and processed in the individual cores of the participating nodes (805). The number of participating nodes and the number of individual cores provided in each of the participating nodes are first confirmed. The ontology matching apparatus for the large-scale biomedical ontologies sets the optimal number of distributions based on the distribution algorithm and the confirmed numbers of the participating nodes and the individual cores. When the numbers of the participating nodes and the individual cores are applied to the distribution algorithm to set the optimal number of distributions, the ontology subsets are divided in consideration of the set optimal number of distributions, and the matching algorithm of the matching library is applied to the divided ontology subsets to generate the matching threads. The generated matching threads include MRs, MJs, and MTs. When the matching threads are generated, each of the generated matching threads is delivered to the corresponding participating node. The individual cores of each of the participating nodes to which the MJs included in the matching threads are allocated perform the matching operations based on the MTs included in the MJs. When the matching operations based on the matching threads are performed in the individual cores of each of the participating nodes, matching results from the matching operations are collected and summed. The ontology matching apparatus for the large-scale biomedical ontologies collects the matching results generated by the matching operations performed in the individual cores of each of the participating nodes, and sums the collected matching results to generate the ontology mapping. The operation 805 may be performed in the same way as the operations 703 to 707 of FIG. 7.

According to the ontology matching apparatus and ontology matching method for the large-scale biomedical ontologies of the present invention, ontology matching operations can be distributed over individual cores of participating nodes and parallel processed, thereby effectively reducing operation resources and operation time required for matching calculation.

The present invention can be implemented as computer readable codes in a computer readable record medium. The computer readable record medium includes all types of record media in which computer readable data is stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An ontology matching apparatus for large-scale biomedical ontologies, the apparatus comprising:
    a processor configured to:
    classify received candidate ontologies into one or more ontology subsets to generate ontology subsets;
    divide the generated ontology subsets by a distribution algorithm, apply a matching algorithm to the divided ontology subsets to generate matching threads, and deliver the generated matching threads to individual cores of participating nodes; and
    collect and sum matching results generated by the individual cores performing matching operations based on the matching threads to generate an ontology mapping,
    wherein in response to receiving the candidate ontologies, the processor is further configured to confirm the number of participating nodes available for matching and the number of individual cores provided in the participating nodes connected to the participating nodes, applies the number of the participating nodes and the number of the individual cores to a distribution algorithm to set the number of distributions, and divides the ontology subsets in consideration of the set number of distributions and applies the matching algorithm to the divided ontology subsets to generate the matching threads including matching requests, matching jobs, and matching tasks.

2. The ontology matching apparatus according to claim 1, wherein the processor is further configured to serializes the generated ontology subsets into a binary form to generate serialized ontology subsets.

3. The ontology matching apparatus according to claim 2, further comprising an ontology storing unit configured to store the serialized ontology subsets, and to provide the serialized ontology subsets that are already stored to the processor when the same candidate ontology as the received candidate ontology is received.

4. The ontology matching apparatus according to claim 3, wherein the processor is further configured to reconfigure the serialized ontology subsets received from the ontology storing unit through deserialization to generate ontology subsets.

5. The ontology matching apparatus according to claim 1, wherein the matching threads include one or more matching requests corresponding to the participating nodes in one-to-one relation, one or more matching jobs corresponding to the individual cores in one-to-one relation provided in the participating nodes corresponding to the matching requests in one-to-one relation, and one or more matching tasks performing the matching operations in the individual cores.

6. The ontology matching apparatus according to claim 5, wherein the relation among the matching requests, the matching jobs, and the matching tasks is calculated by formulae below:

$$MR \leftarrow \sum_{i=1}^{Nodes} MR_i$$

$$MR_i \leftarrow \sum_{j=1}^{Cores} MJ_j$$

$$MJ_j \leftarrow \sum_{k=1}^{Copncepts} MT_k$$

$$MT_k \leftarrow m \times n \mid m \in O_s, n \in O_t$$

wherein $MR_i$ indicates the matching requests allocated to the respective participating nodes, MR indicates a set matching request of $MR_i$ allocated to the participating nodes, $MJ_j$ indicates the matching jobs allocated to the individual cores provided in the participating nodes, and $MT_k$ indicates the matching tasks allocated to the individual cores to perform the matching operations.

7. The ontology matching apparatus according to claim 5, wherein the matching jobs are independent of other matching jobs and the matching requests operating in other participating nodes.

8. The ontology matching apparatus according to claim 1, ontology matching apparatus according to claim 1, wherein collecting and aggregating the matching results of the individual cores including two or more participating nodes is calculated by formulae below $$O_b^{Job} \leftarrow \bigcup_{i=1}^{MT} O_b^i,$$

$$O_b^{Node} \leftarrow \sum_{i=0}^{MJ} O_b^{job=i}$$

$$O_b \leftarrow \sum_{i=1}^{TotalNode} O_b^{Node=i}$$

wherein $O_b^i$ indicates a matching result of a matching task (bridge ontology of the Job matching task), $O_b^{Job}$ indicates an intermediate bridge ontology of a matching job that collected all results of every single matching task in all matching jobs, $O_b^{Node}$ indicates a sum of all intermediate bridge ontologies $O_b^{Job}$ in all matching jobs performed in each of the participating nodes, $O_b^{Job}$ indicates intermediate bridge ontology generated in all nodes, and $O_b$ indicates a bridge ontology that is finally generated and is converted to an ontology mapping result as an output file.

9. The ontology matching apparatus according to claim 8, wherein the matching results calculated by all participating nodes accumulated as one ontology object referred to as a bridge ontology, and
the processor is further configured to aggregate the bridge ontologies that are matching results calculated by the all participating nodes in the distributed environment, and to convert the bridge ontologies to an ontology mapping result as a physical mapping file, and outputs the ontology mapping result.

10. An ontology matching method for large-scale biomedical ontologies, the method comprising:
classifying received candidate ontologies into one or more ontology subsets;
dividing the generated ontology subsets by virtue of a distribution algorithm and applying a matching algorithm to the divided ontology subsets to generate matching threads;
delivering the generated matching threads to individual cores of participating nodes; and
collecting and accumulating matching results generated by the individual cores performing matching operations based on the matching threads to generate an ontology mapping,
wherein in response to receiving the candidate ontologies, the generating of the matching threads comprises:
confirming the number of participating nodes and the number of individual cores provided in the participating nodes available in the distributed environment;
applying the number of the participating nodes and the number of the individual cores to a distribution algorithm to set the number of distributions; and
dividing the ontology subsets in consideration of the set number of distributions and applying the matching algorithm to the divided ontology subsets to generate the matching threads including matching requests, matching jobs, and matching tasks.

11. The ontology matching method according to claim 10, wherein the classifying of the received candidate ontologies into one or more ontology subsets includes serializing the generated ontology subsets to a binary form to generate serialized ontology subsets.

12. The ontology matching method according to claim 11, further comprising storing the serialized ontology subsets, and reconfiguring the serialized ontology subsets that are already stored through deserialization to generate ontology subsets when the same candidate ontology as the received candidate ontology is received.

13. The ontology matching method according to claim 10, wherein the matching threads include one or more matching requests corresponding to the participating nodes in one-to-one relation, one or more matching jobs corresponding to the individual cores in one-to-one relation provided in the participating nodes corresponding to the matching requests in one-to-one relation, and one or more matching tasks performing the matching operations in the individual cores.

14. The ontology matching method according to claim 13, wherein the relation among the matching requests, the matching jobs, and the matching tasks is calculated by formulae below:

$$MR \leftarrow \sum_{i=1}^{Nodes} MR_i$$

$$MR_i \leftarrow \sum_{j=1}^{Cores} MJ_j$$

$$MJ_j \leftarrow \sum_{k=1}^{Copncepts} MT_k$$

$$MT_k \leftarrow m \times n \mid m \in O_s, n \in O_t$$

wherein $MR_i$ indicates the matching requests allocated to the respective participating nodes, MR indicates a set matching request of $MR_i$ allocated to the participating nodes, $MJ_j$ indicates the matching jobs allocated to the individual cores provided in the participating nodes, and $MT_k$ indicates the matching tasks allocated to the individual cores to perform the matching operations.

15. The ontology matching method according to claim 13, wherein the matching jobs are independent of other matching jobs and the matching requests operating in other participating nodes.

16. The ontology matching method according to claim 10, wherein the collecting and summing of the matching results of the aggregating unit in the distributed environment including two or more participating nodes is calculated by formulae below:

$$O_b^{Job} \leftarrow \bigcup_{i=1}^{MT} O_b^i,$$

$$O_b^{Node} \leftarrow \sum_{i=0}^{MJ} O_b^{job=i}$$

$$O_b \leftarrow \sum_{i=1}^{TotalNode} O_b^{Node=i}$$

wherein $O_b^i$ indicates a matching result of a matching task (bridge ontology of the matching task), $O_b^{Job}$ indicates an intermediate bridge ontology of a matching job that collected all results of every single matching task in all matching jobs, $O_b^{Node}$ indicates a sum of all intermediate bridge ontologies $O_b^{Job}$ in all matching jobs performed in each of the participating nodes, $O_b^{Job}$ indicates intermediate bridge ontology generated in all nodes, and $O_b$ indicates a bridge ontology that is finally generated and is converted to an ontology mapping result as an output file.

17. The ontology matching method according to claim 16, wherein the collecting and accumulating of the matching results generated by the individual cores performing the matching operations based on the matching threads to generate the ontology mapping includes summing the bridge ontologies that are matching results calculated by the all participating nodes, converting the bridge ontologies to an ontology mapping result as a physical mapping file, and outputting the ontology mapping result.

* * * * *